(12) United States Patent
Brivio et al.

(10) Patent No.: US 7,670,340 B2
(45) Date of Patent: Mar. 2, 2010

(54) ENDOMEDULLARY NAIL FOR THE TREATMENT OF PROXIMAL FEMUR FRACTURES

(75) Inventors: Lodovico Renzi Brivio, Verona (IT); Franco Lavini, Verona (IT); Michele Coati, San Pietro in Cariano (IT); Graziano Marini, Castel d'Azzano (IT); Luigi Rossi, Peschiera del Garda (IT)

(73) Assignee: Orthofix International B.V., Amsterdam (NL)

( * ) Notice: Subject to any disclaimer, the term of this patent is extended or adjusted under 35 U.S.C. 154(b) by 1167 days.

(21) Appl. No.: 11/233,475

(22) Filed: Sep. 21, 2005

(65) Prior Publication Data

US 2006/0069392 A1    Mar. 30, 2006

(30) Foreign Application Priority Data

Sep. 27, 2004    (EP)    .................... 04425717

(51) Int. Cl.
*A61B 17/72* (2006.01)
(52) U.S. Cl. .............. 606/64; 606/62; 606/67
(58) Field of Classification Search ............. 606/62–68, 606/89, 96
See application file for complete search history.

(56) References Cited

U.S. PATENT DOCUMENTS

| | | | | |
|---|---|---|---|---|
| 4,640,271 A | * | 2/1987 | Lower | 606/65 |
| 5,531,748 A | * | 7/1996 | de la Caffiniere | 606/62 |
| 5,549,610 A | * | 8/1996 | Russell et al. | 606/64 |
| 6,030,162 A | * | 2/2000 | Huebner | 411/413 |
| 6,126,661 A | * | 10/2000 | Faccioli et al. | 606/64 |
| 2003/0004514 A1 | * | 1/2003 | Frigg et al. | 606/62 |
| 2005/0055023 A1 | * | 3/2005 | Sohngen et al. | 606/62 |

FOREIGN PATENT DOCUMENTS

| | | |
|---|---|---|
| EP | 0 715 832 A2 | 6/1996 |
| JP | 2002-253566 | 9/2002 |

* cited by examiner

*Primary Examiner*—Eduardo C Robert
*Assistant Examiner*—Steven J Cotroneo
(74) *Attorney, Agent, or Firm*—Seed IP Law Group PLLC

(57) ABSTRACT

An endomedullary nail for the treatment of proximal femur fractures, comprising an elongate body (12) having a proximal portion (14) and a distal portion (16). The proximal portion (14) has a first and a second hole (20, 21) for a respective cephalic screw (22, 23, 24, 25), each having a transversal axis to the axis of the proximal portion (14). The first hole (20) is split into two passages each having a respective axis (A, B) with a predetermined angle relationship with respect to the axis (C) of the second hole (21). The passages (30, 31) are arranged to be selectively engaged by a respective cephalic screw (22, 24).

17 Claims, 5 Drawing Sheets

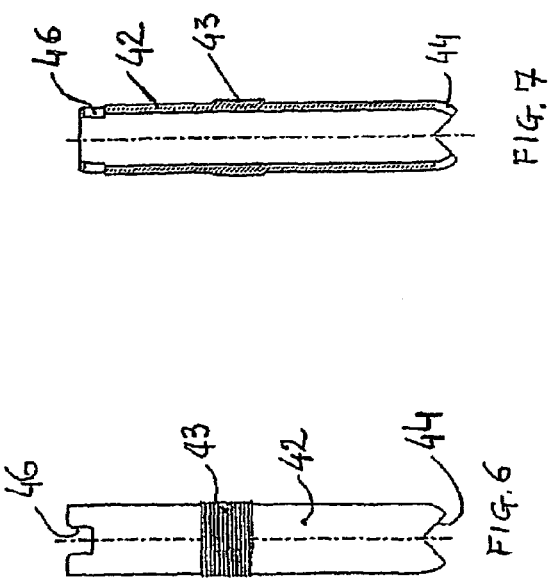
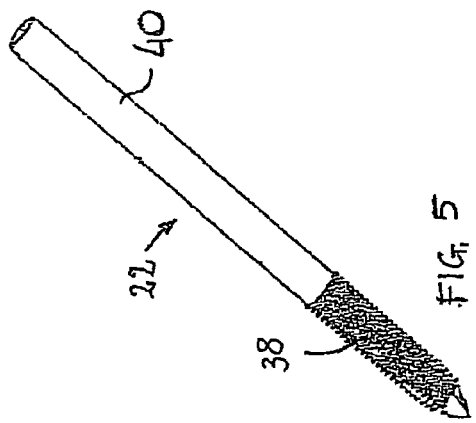
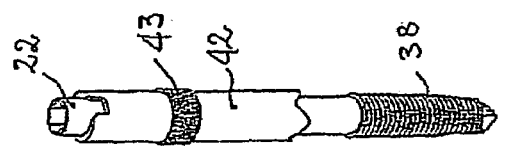

ENDOMEDULLARY NAIL FOR THE TREATMENT OF PROXIMAL FEMUR FRACTURES

BACKGROUND OF THE INVENTION

1. Field of the Invention

The present invention generally relates to an endomedullary nail for the treatment of proximal femur fractures, such as for example pertrochanteric fractures whose fissure extends from the lesser to the greater trochanter, medial fractures and at the base of the femur neck, and the like.

The nail comprises an elongate body having a proximal portion and a distal portion. In the proximal portion thereof, the nail also comprises a first and a second hole, each having a transversal axis to the proximal portion axis for a corresponding cephalic screw.

The present invention also relates to a device for the treatment of proximal femur fractures comprising the above-mentioned nail and the corresponding cephalic screws.

2. Description of the Related Art

The now widespread use of endomedullary nails as above for the osteosynthesis of proximal femur fractures is known.

Fracture stabilisation is mainly obtained by means of two cephalic screws. The latter are inserted transversally to the nail into two respective circular holes of the proximal portion so as to cross the femur neck spongiosis up to reach the femur head in order to allow a mutual stump compression.

The cephalic screw arrangement and orientation with respect to the endomedullary nail substantially depend on the fracture type. In particular, according to the seriousness, the femur neck composing structure, the patient's age and the trauma type, fragments and fissures, which are different from each other, can be formed.

In most known nails, the two holes for cephalic screws have parallel axes.

On the contrary, for other types of trauma, mainly in case of serious pertrochanteric fractures, wherein it is necessary to ensure a certain nail and screw staticity, the two proximal holes have convergent axes. Therefore cephalic screws, once being inserted into the femur neck, mutually converge ensuring a high stabilisation thereof and the head. A nail with convergent-axis holes is known for example from the patent EP 0 853 923 in the name of the Applicant.

A further intramedullary femoral nail for the treatment of fractures is known from U.S. Pat. No. 5,549,610A in the name of RUSSEL et al. The nail includes three proximal locking screw passageways, two parallel upwardly oblique passageways and a single downwardly oblique passageway. The two parallel upwardly oblique passageways are suitable for the insertion of two cephalic screws in the head of the femur in reconstruction mode and the single downwardly oblique passageway is suitable for insertion of one screw transversally in the neck of the femur in a femoral mode.

Another nail is known from the Japanese patent application JP 2002253566 in the name of MIZUHO. This nail comprises in its own proximal portion opposite slots wherein from 2 to 6 screws can be inserted. The screws are inserted in mutual crossing in the opposite slots in mutual engagement. A tip is provided which is inserted in the head portion of the nail and it presses the screws against each other.

However, known nails, although ensuring a complete fracture stabilisation, have recognised drawbacks being not yet overcome.

The main drawback is that, just to ensure the containment of a particular type of fracture, the nail and cephalic screw configuration is substantially predetermined, restraining and limiting the possibility to change the endomedullary nail application in different traumatic situations.

It results that the use of known endomedullary nails for the stabilisation of fractures having a different nature is considerably limited, since this would inevitably involve a wrong arrangement and orientation of the two cephalic screws.

This drawback is even more serious when considering that, according to the type of femur fracture, a surgeon is obliged to exclusively choose preliminarily, i.e. before the intervention, the endomedullary nail to be used and he cannot change the orientation of the two cephalic screws when the nails has already been implanted.

The aim of the present invention is that of providing an endomedullary nail overcoming the above-mentioned drawbacks in order to have a higher application versatility and, particularly, allowing a surgeon to change the cephalic screw configuration when operating during the surgical intervention.

A further aim of the invention is that of providing an endomedullary nail allowing a surgeon to change the cephalic screw configuration without requiring the nail removal from the medullar cavity.

Another aim of the present invention is that of providing a nail allowing to obtain at least two different screws fixing configurations.

BRIEF SUMMARY OF THE INVENTION

A first embodiment of the invention relates to an endomedullary nail for the treatment of proximal femur fractures, comprising:

an elongate body having a proximal portion and a distal portion, the proximal portion having a first and a second hole for a respective cephalic screw;

each hole having a transversal axis with respect to the axis of the proximal portion; and wherein the first hole is split into two passages each having a respective axis with a predetermined angle relationship with respect to the axis of the second hole;

said passages being arranged to be selectively engaged by a respective cephalic screw.

The invention further relates to a device for the treatment of proximal femur fractures comprising:

an endomedullary nail having a proximal portion and a distal portion, the proximal portion having a first and a second hole each having a transversal axis with respect to the axis of the proximal portion;

cephalic screws suitable for insertion into said first and a second hole of the endomedullary nail, respectively; and the first hole of the nail being split into two passages each having a respective axis with a predetermined angle relationship with respect to the axis of the second hole, said passages being arranged to be selectively engaged by one of the cephalic screws.

The features and advantages of the endomedullary nail according to the invention will be apparent from the following description of an embodiment thereof given by way of non limiting example with reference to the attached drawings.

BRIEF DESCRIPTION OF THE SEVERAL VIEWS OF THE DRAWING(S)

FIG. 3 shows a first cephalic screw for the endomedullary nail of FIG. 1.

FIG. 4 shows a second cephalic screw with sliding sleeve for the endomedullary nail of FIG. 1.

FIG. 5 shows the cephalic screw of FIG. 4.

FIG. 6 shows in enlarged scale the sleeve of FIG. 4.

FIG. 7 shows a cross section of the sleeve of FIG. 6.

DETAILED DESCRIPTION OF THE INVENTION

Figure 1:
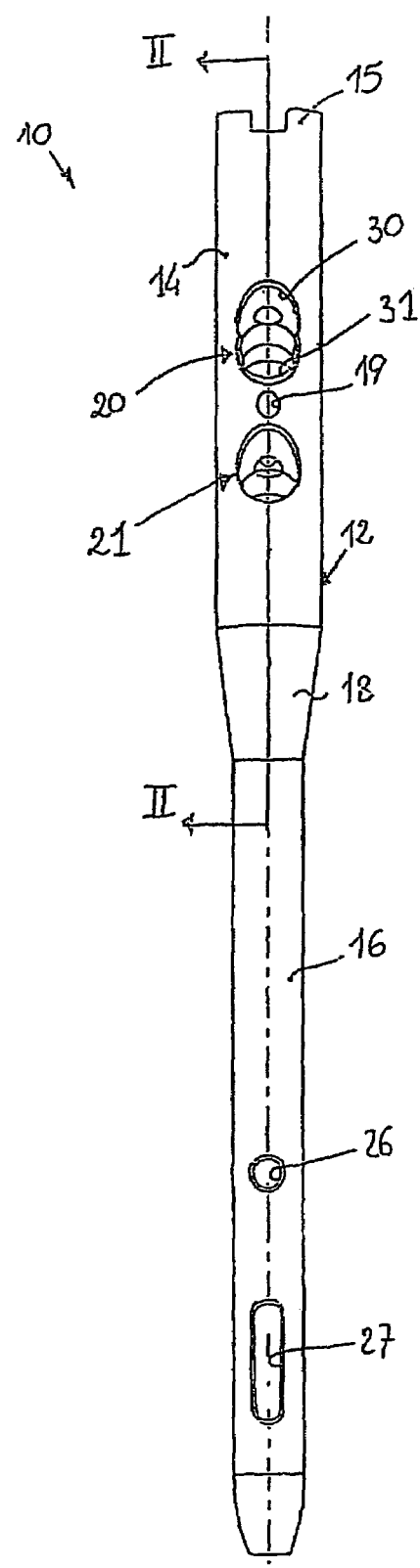
FIG. 1 is a front view of the nail according to the present invention.

With reference to the attached drawings, an endomedullary nail for the treatment of proximal femur fractures according to the present invention is generally indicated with the reference number 10

The nail 10 comprises an elongate body 12, preferably made of titanium, having a head 15, a proximal portion 14 and a distal portion 16. The two portions 14 and 16, suitable for insertion into the neck and into the femur diaphysis respectively, preferably forms an angle, in this case an angle of about 4-5° in order to fit the femur anatomical shape.

The proximal portion 14 also comprises, in correspondence with the head 15 of the nail 10, a seat 17 (FIG. 2) for the insertion of corresponding instruments for the nail 10 manipulation, such as for example the one being described in said patent EP 0 853 923 in the name of the Applicant.

In this specific case, the proximal portion 14 has a higher diameter than the distal portion 16 and it is connected thereto by means of a substantially cone-shaped connecting portion 18.

Figure 8:
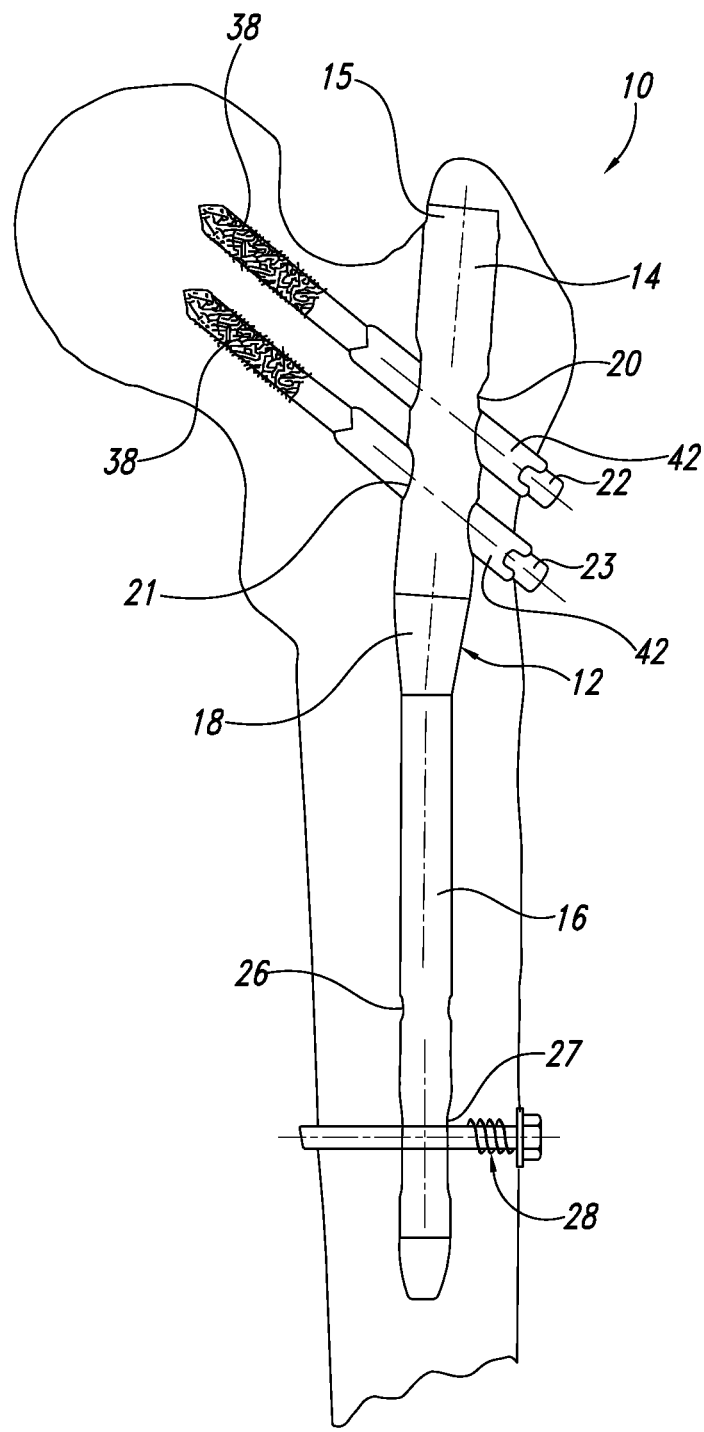
FIG. 8 shows the nail of FIG. 1 in a first configuration.
Figure 9:
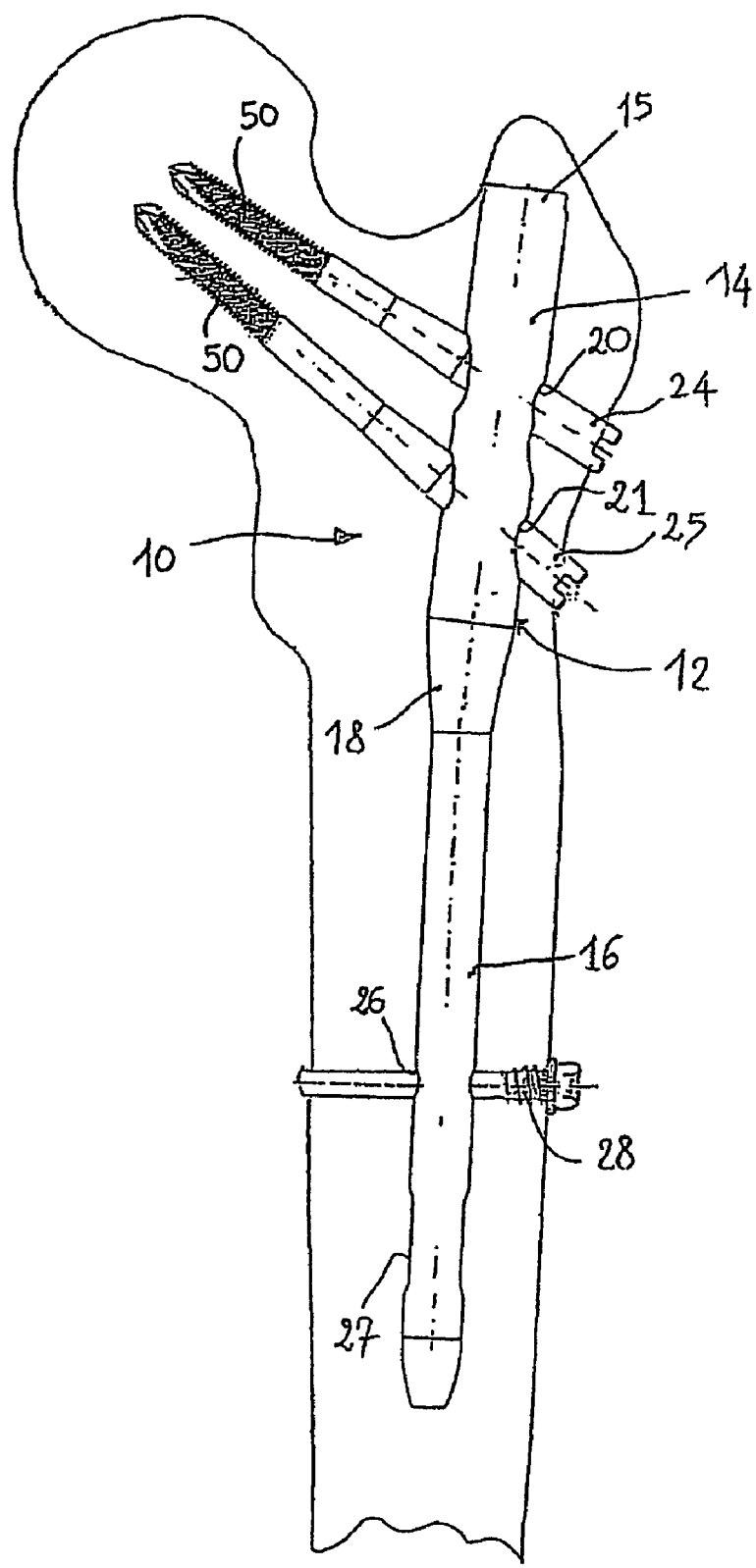
FIG. 9 shows the nail of FIG. 1 in a second configuration.

In the distal portion 16 the endomedullary nail 10 comprises a hole 26 and a slot 27 for corresponding distal pins 28 (FIGS. 8 and 9).

In the proximal portion 14 the endomedullary nail 10 comprises, starting from the head 15, a first and a second hole 20 and 21 respectively for receiving and hosting corresponding cephalic screws 22, 23, 24, 25 (FIGS. 3, 4, 5, 8, 9). A cephalic screw is a special screw, which is inserted through the nail so that it extends across the fracture of the bone and into the femular head. Accordingly the cephalic screw has at least a threaded end that engages the femular head. It is also clear that even other kind of screws may be used with the nail of the present invention.

A third hole 19 is obtained in this specific case between the first and the second hole 20, 21 for the insertion of a wire for controlling the position and depth of cephalic screws 22, 23, 24 and 25.

According to the invention, while the second proximal hole 21 has a substantially circular cross section and it extends with an axis C sloping on the axis X of the proximal portion 14, the first hole 20 is split into two passages being arranged to be selectively engaged by a respective cephalic screw 22, 24 and they have an axis with a predetermined angle relationship with respect to the second hole 21, in order to obtain a different orientation of the cephalic screws being inserted therein. In other words, the first hole is formed from a slot defined by two interfering passages.

Preferably the first hole 20 has a substantially "eight-shaped" cross section defined by two passages 30 and 31, which are adjacent and longitudinally open the one into the other, in other words said passages 30 and 31, composing said first proximal hole 20, are each substantially cylinder-shaped and longitudinally interfering.

Preferably the two passages 30, 31 have respective convergent axes A and B with a predetermined convergence axis and intended to be turned towards the femur head.

Figures 2, 2A:
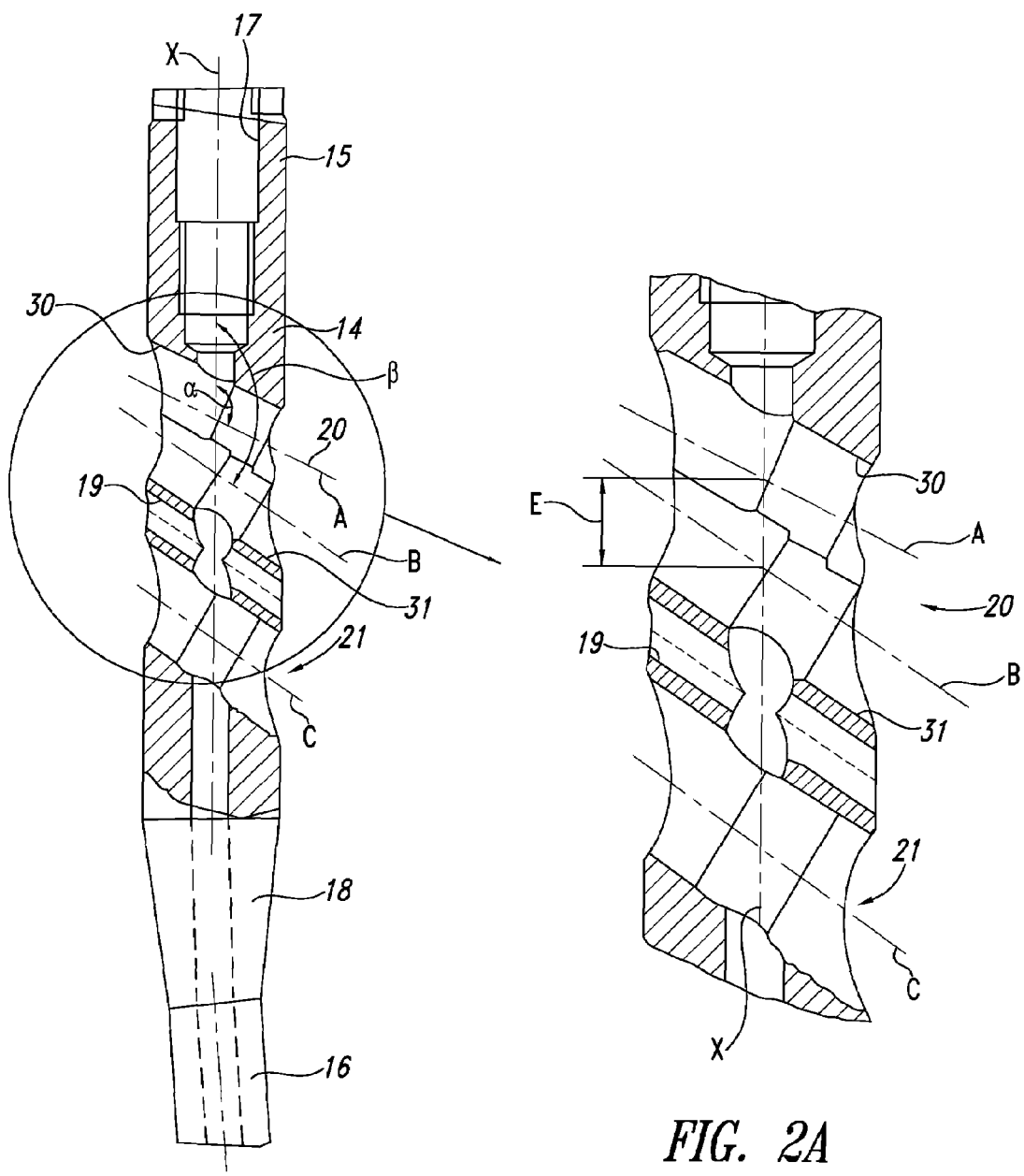
FIG. 2 is an enlarged-scale cross section along the line II-II of FIG. 1.
FIG. 2a shows a further enlarged detail of FIG. 2.

In particular, with reference to FIGS. 2 and 2a, the passage 30, in this case the closest to the head 15 of the nail 10, has an axis A forming an angle with the axis C of the second hole 21, while the second passage 31, i.e. the farthest from the head 15 of the nail 10, has an axis B being substantially parallel to the axis C of the second hole 21.

In the case of the shown solution, the first passage 30 forms an angle α of about 115° with the axis X of the proximal portion 14 of the endomedullary nail 10, while the second passage 31, and similarly the second proximal hole 21, form and angle β of about 123° with the axis X of the proximal portion 14 of the nail 10.

Therefore, the first passage 30 and the second passage 31 are convergent towards the femur head with a convergence angle of about 8°.

In the specific case of the solution shown in the drawings, both passages 30, 31 have a diameter of 8.5 mm and the distance E between the corresponding axes A and B, measured along the axis X of the proximal portion 14, is of some millimetres, about 2 mm.

As it will be better seen hereafter, both the two passages 30, 31 and the second hole 21 are equipped with a thread for the cephalic screw engagement.

As above disclosed, the presence of the two passages 30, 31 with a differently sloping axis allows a single endomedullary nail 10 to be alternately configured according to two different configurations.

In this specific case, in a first configuration (FIG. 8), the two screws 22, 23 are inserted into the second passage 31 of the first hole 20 and into the second hole 21 respectively, in order to be substantially parallel.

In a second configuration (FIG. 9), the two screws 24, 25 are inserted into the first passage 30 of the first hole 20 and into the second hole 21 respectively, in order to converge towards the femur head.

According to another aspect, the present invention also relates to a device for the treatment of proximal femur fractures comprising the above-described endomedullary nail 10 and the cephalic screws 22, 23, 24, 25.

In particular, according to the invention the device comprises four cephalic screws 22, 23, 24, 25 which will be described hereafter.

In the first configuration, i.e. the parallel-axis one, the two cephalic screws 22, 23 are of the so-called dynamic type, i.e. screws, which can slide with respect to the nail 10.

In particular, the screws 22, 23 (FIGS. 4, 5, 6, 7) comprise a single self-threading thread 38 self-penetrating into the femur head, and a cylinder-shaped stem 40 equipped, in the head area, with an embedded hexagon for a convenient working tool.

Moreover the embedded hexagon wall or the screw cannulation is preferably threaded in order to allow the tool to be eventually fixed in an extraction step of the cephalic screws from the nail.

The device also comprises a sleeve 42 wherein the stem 40 of the screw 22, 23 is slidingly inserted.

The sleeve 42 comprises, in a central area, an external thread 43 for being screwed into the proximal holes 20, 21; moreover sharp profiles 44 can be obtained at a first end of the sleeve 42 in order to allow the advance thereof into the bone and, at a second end, a screwdriver slot 46 for the connection to a convenient instrument.

In this specific case, the thread 43 of the sleeve 42 has an apparent pitch corresponding to half the pitch of the self-threading thread 38 of the screw 22, 23 to penetrate into the bone.

The arrangement of the two cephalic screws 22, 23 and of the sleeve 42 in the parallel-axis configuration is performed as follows.

After inserting the nail 10 into the medullar cavity, the cephalic screws 22, 23 are inserted into the second passage 31 and into the second hole 21 respectively together with the sleeve 42 and screwed into the femur head. Therefore the sleeve 42 is inserted together with the screws 22, 23 and screwed into the passage 31 and into the hole 21.

It must be noted that, doing so, only the sleeve 42 is screwed into the nail 10, ensuring certain dynamicity and movement elasticity to the screws 22, 23 with respect to the endomedullary nail 10.

At a second point, the pin 28 is preferably inserted into the slot 27 in order to prevent the nail 10 rotation.

In the second configuration (FIG. 9), i.e. the convergent-axis one, the device according to the invention comprises two cephalic screws 24, 25 of the so-called static type, suitable to be screwed both into the nail 10 and into the bone.

In particular, they are screws 24, 25 (FIG. 3) having a uniform resistance, equipped each with a first self-threading thread 50 self-penetrating into the femur head and with a second thread 51 to be screwed with the nail 10. It must also be noted that the screws 24, 25 have a bulge 55 in correspondence with the connection area with the nail 10 to allow the screwing thereof.

In this case too, the screws are equipped with an embedded hexagon preferably equipped with the corresponding thread.

The arrangement of the two cephalic screws 24, 25 in the convergent-axis configuration is performed as follows.

After inserting the nail 10 into the medullar cavity, the two cephalic screws 24, 25 are directly inserted into the first passage 30 and into the second hole 21 respectively. Afterwards, the distal pin 28 is inserted into the hole 26.

In this case too, the second thread 51 has an apparent pitch corresponding to half the pitch of the first thread 50 to penetrate into the bone, allowing the screw to constantly advance into the bone and into the nail 10. A stiff constraint is thus obtained between the two screws 24, 25 and the nail 10.

The main advantage of the endomedullary nail according to the present invention is that a single endomedullary nail is used to obtain two different cephalic screw configurations, such as for example a first parallel-axis screws configuration and another convergent-axis screws configuration.

Moreover, since the two passages 30, 31 are interfering and open the one towards the other to form a single slot having an "eight-shaped" cross section, it advantageously results that the cephalic screw, when inserted into one passage or into the other, keeps its axial position along the nail proximal portion.

Therefore, passing from a configuration to the other, the distance between the two cephalic screws, conveniently adapted to the femur neck size, is substantially constant.

This allows only a screw angle orientation change to be obtained between the two configurations. Therefore each screw, in both configurations, is kept in a position substantially corresponding to the position it would have had in a traditional nail equipped with two circular holes.

Moreover, due to the integration in a single slot, the nail 10 is not excessively weakened by the presence of the double passage.

Another advantage is that a surgeon can choose directly in the operating room, according to the situation he is facing, if the screw 22, 24 is to be inserted into one passage or into the other 30, 31 of the first hole 20, in order to change the angle relationship thereof with respect to the other screw 23 and 25 of the second hole 21, and without removing the nail 10 from the medullar cavity.

In particular, the choice of the two predetermined angles of inclination (about 115° and 123° respectively) of the two passages 30, 31 and of the second hole 21 for the static and dynamic configuration respectively, is particularly suitable for a complete containment of a pertrochanteric fracture.

Another advantage of the present invention is that, according to the screw configuration, a static or dynamic device for the treatment of proximal femur fractures can be obtained by means of a single nail.

In fact, when it is necessary, in response to specific stresses, to ensure certain device dynamicity, the sliding cephalic screws equipped with the corresponding sleeve can be inserted into the parallel-axis holes.

It must be noted that it is possible to obtain also the dynamicity of the nail distal portion. It is obtained by inserting a single pin into the distal slot. In fact it does not constrain a nail movement, caused for example by a possible axial stress.

Similarly, when absolute stress stiffness is required, the double-threaded screws are screwed into the convergent-axis holes.

It must be noted in this case too that, in the convergent-axis configuration, the staticity is kept also at the level of distal portion 16 of the nail 10, since the pin 28 is inserted only into the circular hole 26.

Therefore, the choice for stability or dynamicity, not only for the femur cephalic portion, but also for the femur central portion, or diaphysis, is thus performed according to the type of fracture and it is not constrained by the device being used.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An endomedullary nail for the treatment of proximal femur fractures, comprising:
   an elongate body having a proximal portion and a distal portion, the proximal portion having a first and a second hole for a respective cephalic screw;
   each hole having a transversal axis with respect to an axis of the proximal portion; wherein
   the first hole is substantially eight-shaped in cross section and is split into two passages which open into each other all along their longitudinal extension; and wherein
   each passage has a different respective axis with a predetermined angle relationship with respect to the axis of the second hole; a first of said passages has the axis forming an angle with the axis of the second hole, while a second of said passages has the axis being substantially parallel to the axis of the second hole;
   the axis of the first passage intersecting the axis of the second passage at an angle of about 8°;
   each of said passages being configured and arranged to be selectively engaged by a respective cephalic screw in combination with said second hole being engaged by another respective cephalic screw.

2. The nail of claim 1 wherein the first passage forms an angle of about 115° with the axis of the proximal portion.

3. The nail of claim 1 wherein the second passage forms an angle of about 123° with the axis of the proximal portion.

4. The nail of claim 1 wherein the distance between the axis of the first passage and the axis of the second passage measured along the axis of the proximal portion corresponds to about 2 mm.

5. The nail of claim 1 wherein both the two passages and the second hole are equipped with a thread for the cephalic screw engagement.

6. The nail of claim 1 wherein the passages are cylindrical-shaped.

7. A device for the treatment of proximal femur fractures comprising:
   an endomedullary nail having a proximal portion and a distal portion, the proximal portion having a first and a second hole each having a transversal axis with respect to an axis of the proximal portion;
   cephalic screws suitable for insertion into said first and a second hole of the endomedullary nail, respectively;
   the first hole of the nail being substantially eight-shaped in cross section and split into two passages which open into each other all along their longitudinal extension, each passage having a different respective axis with a predetermined angle relationship with respect to the axis of the second hole, the axis of the first passage forming with the axis of the second passage an angle of about 8°, said passages being arranged to be selectively engaged by one of the cephalic screws, wherein each selective engagement of said passages is arranged in combination with the second hole being engaged by another one of the cephalic screws.

8. The device of claim 7 comprising two first cephalic screws which are suitable for insertion in the second passage of the first hole and in the second hole respectively to obtain a first configuration and two second screws which are suitable for insertion in the first passage of the first hole and in the second hole respectively to obtain a second configuration alternately to the first configuration.

9. The device of claim 8 wherein a first of said passages has the axis forming an angle with the axis of the second hole, while a second of said passages has the axis being substantially parallel to the axis of the second hole.

10. The device of claim 9 wherein each of the two first cephalic screws has a self-threading thread to be screwed into the bone and a smooth stem to be slidingly inserted into the second passage of the first hole and into the second proximal hole respectively in order to be positioned parallel to each other obtaining a dynamic configuration.

11. The device of claim 9 wherein each of the two second cephalic screws has a first self-threading thread to be screwed into the bone and a second thread to be screwed into the first passage of the first hole and into the second proximal hole respectively in order to be positioned convergent to each other obtaining a static configuration.

12. The device of claim 10 wherein it comprises two sleeves having an external thread to be screwed into the second passage of the first hole and into the second proximal hole respectively and wherein the stems of the first cephalic screws are slidingly inserted.

13. The device of claim 12 wherein each sleeve comprises sharp profiles to advance into the bone.

14. The device of claim 12 wherein the external thread of the sleeves has an apparent pitch corresponding to half the pitch of the self-threading thread of the first screw to penetrate into the bone.

15. The device of claim 11 wherein the second thread of the second cephalic screws has an apparent pitch corresponding to half the pitch of the first self-threading thread.

16. An endomedullary nail for the treatment of femur fractures, comprising:
   an elongate body having a proximal portion and a distal portion;
   an eight-shaped slot formed in said proximal portion by two interfering passages for receiving corresponding fixing respective screws in each passage;
   a hole in said proximal portion;
   each of said passages having a respective axis with a predetermined angle relationship with respect to the axis of the nail and to the axis of said hole in said proximal portion, wherein the respective axis of each of said passages being a transversal axis with respect to an axis of said proximal portion, the axis of the first passage defining with the axis of the second passage an angle of about 8°, each of said passages being configured to selectively receive a respective fixing screw in combination with said hole in the proximal portion receiving another respective screw.

17. A device for the treatment of proximal femur fractures comprising:
   an endomedullary nail having a proximal portion and a distal portion, the proximal portion having a first and a second hole each having a transversal axis to an axis of the proximal portion, and
   cephalic screws suitable for insertion into said first and a second hole of the endomedullary nail, respectively;
   the first hole of the nail having an eight-shaped cross section defined by two cylindrical passages which are adjacent and which open into each other all along their longitudinal extension;
   each of said passages having a different respective axis with a predetermined angle relationship with respect to the axis of the second hole, said passages being arranged to be alternately engaged by one of the cephalic screws, the angle relationship of the axis of the first passage with respect to the axis of the second passage being about 8°, and wherein
   two first cephalic screws being suitable for insertion in the second passage of the first hole and in the second hole, respectively, to obtain a first configuration wherein the two first cephalic screws engage the second passage in combination with the second hole; and
   two second screws being suitable for insertion in the first passage of the first hole and in the second hole, respectively, to obtain a second configuration alternative to the first configuration wherein the two second cephalic screws engage the first passage in combination with the second hole.

* * * * *